United States Patent
Matsui

(10) Patent No.: US 8,765,294 B2
(45) Date of Patent: Jul. 1, 2014

(54) ASYMMETRIC TYPE BF$_3$ COMPLEX

(75) Inventor: Masaki Matsui, Susono (JP)

(73) Assignee: Toyota Jidosha Kabushiki Kaisha, Toyota-shi, Aichi-ken (JP)

(*) Notice: Subject to any disclaimer, the term of this patent is extended or adjusted under 35 U.S.C. 154(b) by 740 days.

(21) Appl. No.: 12/601,277

(22) PCT Filed: Apr. 21, 2008

(86) PCT No.: PCT/JP2008/057691
§ 371 (c)(1), (2), (4) Date: Jun. 10, 2010

(87) PCT Pub. No.: WO2008/149612
PCT Pub. Date: Dec. 11, 2008

(65) Prior Publication Data
US 2010/0291436 A1    Nov. 18, 2010

(30) Foreign Application Priority Data
May 29, 2007 (JP) ................... 2007-142401

(51) Int. Cl.
*H01M 6/04*    (2006.01)

(52) U.S. Cl.
USPC .......................................... 429/188; 252/62.2

(58) Field of Classification Search
USPC ............... 429/188, 338, 342, 343; 252/521.4, 252/62.2
See application file for complete search history.

(56) References Cited

U.S. PATENT DOCUMENTS 3,915,743 A * 10/1975 Lauck ........................... 429/326
4,518,798 A    5/1985 Kramer et al.

(Continued)

FOREIGN PATENT DOCUMENTS

DE     739 579       9/1943
EP     0 105 699     4/1984

(Continued)

OTHER PUBLICATIONS

Gajewski, J.J. et al., "Equilibrium Constants between Boron Trifluoride Etherate and Carbonyl Compounds in Chloroform Solution," Organic Letters, vol. 2, No. 18, (2000), pp. 2813-2815.

(Continued)

*Primary Examiner* — Joseph S Del Sole
*Assistant Examiner* — David N Brown, II
(74) *Attorney, Agent, or Firm* — Finnegan, Henderson, Farabow, Garrett & Dunner, LLP

(57) ABSTRACT

A main object is to provide an asymmetric type BF$_3$ complex which is useful as a solvent for a liquid electrolyte for electrochemical device, in which the liquid electrolyte has a wide potential window and is particularly excellent in oxidation resistance. To attain the object, an asymmetric type BF$_3$ complex is represented by the following general formula (1):

General Formula (1)

$$R_1-O-C(=O\text{-}BF_3)-R_2$$

(in the general formula (1), each of R$_1$ and R$_2$ is an alkyl group having 1 to 6 carbon atoms and may be the same or different, and R$_1$ and R$_2$ may be branched or may form a ring).

4 Claims, 3 Drawing Sheets

(56) References Cited

U.S. PATENT DOCUMENTS

| | | | | |
|---|---|---|---|---|
| 6,045,948 A | * | 4/2000 | Wang et al. | 429/231.95 |
| 2001/0053474 A1 | | 12/2001 | Oura et al. | |

FOREIGN PATENT DOCUMENTS

| | | |
|---|---|---|
| JP | 43-12830 | 5/1968 |
| JP | 59-82337 | 5/1984 |
| JP | 11-149943 | 6/1999 |
| JP | 2000-138072 | 5/2000 |
| JP | 2005-510017 | 4/2005 |
| KR | 10-0408085 | 11/2003 |

OTHER PUBLICATIONS

Borovikov, Y.Y. et al., "Dipole Moments of Complexes of Tin Tetrachloride and Boron Trifluoride With Ethers and Esters," Journal of General Chemistry of the USSR, vol. 50, No. 11, (1990), pp. 2049-2052.

Landolph, F.R., "Ueber die Einwirkung des Fluorbors urf auf organische sauerstoff haltige Substanzen u auf Kohlenwasserstoffe," Chemie Berichte, vol. 10, No. 2, (1877), pp. 1312-1314.

Extended European Search Report for EP Appl. No. 08740733.4 dated Jul. 5, 2011.

H. Bowlus et al., "The Action of Boron Fluoride on Organic Compounds," Journal of the American Chemical Society, vol. 53, pp. 3835-3840 (1931).

F. Lewis et al., "Lewis Acid Catalysis of Photochemical Reactions. 4. Selective Isomerization of Cinnamic Esters," Journal of the American Chemical Society, vol. 108, pp. 3005-3015 (1986).

* cited by examiner

ASYMMETRIC TYPE $BF_3$ COMPLEX

CROSS-REFERENCE TO RELATED APPLICATIONS

This application is a national phase application of International Application No. PCT/JP2008/057691, filed Apr. 21, 2008, and claims the priority of Japanese Application No. 2007-142401, filed May 29, 2007, the contents of both of which are incorporated herein by reference.

TECHNICAL FIELD

The present invention relates to an asymmetric type $BF_3$ complex which can provide a liquid electrolyte for electrochemical device, in which the liquid electrolyte has a wide potential window and is particularly excellent in oxidation resistance.

BACKGROUND ART

Conventionally, liquid electrolytes having a lithium salt dissolved in a non-aqueous solvent have been used as liquid electrolytes used in lithium secondary batteries. Furthermore, mixed solvents of ethylene carbonate, propylene carbonate, diethyl carbonates etc. are generally used as the non-aqueous solvent.

These carbonate-based solvents are generally used as the non-aqueous solvent, but suffer from a problem of poor oxidation resistance. Accordingly, there is a demand for hardly oxidized liquid electrolytes, from the viewpoint of improving the performance of lithium secondary batteries. Generally, liquid electrolytes are preferably those hardly undergoing oxidation and reduction; in order words, liquid electrolytes with a wide potential window are desired.

On the other hand, lithium secondary batteries having a $BF_3$ complex added to a liquid electrolyte are known. For example, Patent Document 1 discloses a non-aqueous lithium battery using a $BF_3$ complex as a capacity reduction rate-suppressing additive. Patent Document 1 addresses prevention of a lithium secondary battery from reducing its capacity caused during long-term use by using a $BF_3$ complex as an additive. Patent Document 2 discloses a non-aqueous electrolyte secondary battery comprising a Werner-type complex of boron trifluoride. Patent Document 2 aims at preventing a film of lithium halide such as LiF from generating on the surface of an anode by using a $BF_3$ complex as an additive, thereby suppressing an increase in battery impedance.

In both of Patent Documents 1 and 2, however, the $BF_3$ complex is used absolutely as an additive, and the amount of the complex used is very small. Specifically, the amount of the $BF_3$ complex is about 1 to 5% by weight based on the electrolyte in Patent Document 1, and the amount of the $BF_3$ complex is about 0.5 to 5% by weight based on the whole of the liquid electrolyte in Patent Document 2. Furthermore, in Patent Documents 1 and 2, there is absolutely no description to the effect that the performance of the lithium secondary battery is improved by widening the potential window of the liquid electrolyte.

Patent Document 3 discloses an electrode active material for lithium secondary battery, which further comprises an amphoteric compound such as a $BF_3$ complex in an electrode active material.

Patent Document 1: Japanese Patent Application Laid-Open (JP-A) No. H11-149943
Patent Document 2: JP-A No. 2000-138072
Patent Document 3: JP-A No. 2005-510017

DISCLOSURE OF THE INVENTION

Problems to be Solved by the Invention

The present invention is achieved in view of the above-mentioned situation. A main object of the present invention is to provide an asymmetric type $BF_3$ complex which is useful as a solvent for a liquid electrolyte for electrochemical device, in which the liquid electrolyte has a wide potential window and is particularly excellent in oxidation resistance.

Means for Solving the Problems

To solve the above-mentioned problems, the present invention provides an asymmetric type $BF_3$ complex represented by the following general formula (1):

[Chemical Formula 1]

General Formula (1)

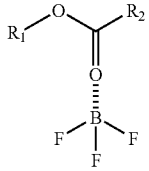

(in the general formula (1), each of $R_1$ and $R_2$ is an alkyl group having 1 to 6 carbon atoms and may be the same or different, and $R_1$ and $R_2$ may be branched or may form a ring).

In the present invention, an organic molecule (ester) which coordinates to an unoccupied orbital of boron of $BF_3$ has an asymmetric structure to a B—O binding. Thus, a crystal structure is unlikely to be formed, and a complex having a lower melting point and a lower heat of fusion compare to those of similar symmetric type $BF_3$ complex can be obtained. Thus, the asymmetric type $BF_3$ complex of the present invention is useful, for example, as a solvent for a liquid electrolyte for electrochemical device.

In the above-mentioned invention, the asymmetric type $BF_3$ complex is preferably a kind of complex selected from the group consisting of the following structural formulae (1a) to (1c). This is because such asymmetric type $BF_3$ complex is useful as a solvent for a liquid electrolyte for electrochemical device.

[Chemical Formula 2]

Structural Formula (1a)

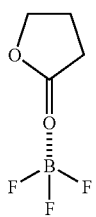

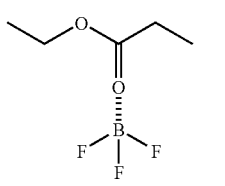

Structural Formula (1b)

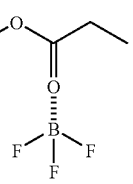

Structural Formula (1c)

Further, the present invention provides a liquid electrolyte for electrochemical device which comprises the above-mentioned asymmetric type $BF_3$ complex as a solvent. According to the present invention, a liquid electrolyte for electrochemical device having a wide potential window can be obtained by using the asymmetric type $BF_3$ complex as a solvent.

Moreover, the present invention provides a liquid electrolyte for electrochemical device comprising an asymmetric type $BF_3$ complex represented by the following general formula (2) as a solvent:

[Chemical Formula 3]

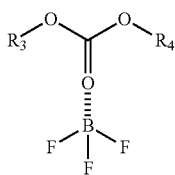

General Formula (2)

(in the general formula (2), each of $R_3$ and $R_4$ is an alkyl group having 1 to 5 carbon atoms and is a different alkyl group).

According to the present invention, a liquid electrolyte for electrochemical device having a wide potential window can be obtained by using the asymmetric type $BF_3$ complex as a solvent.

In the above-mentioned invention, the asymmetric type $BF_3$ complex is preferably a complex represented by the below-mentioned structural formula (2a). This is because such asymmetric type $BF_3$ complex is useful as a solvent for a liquid electrolyte for electrochemical device.

[Chemical Formula 4]

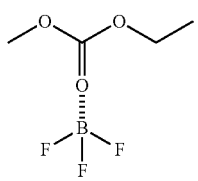

Structural Formula (2a)

Further, the present invention provides a lithium secondary battery comprising: a cathode layer containing a cathode active material, an anode layer containing an anode active material, a separator provided between the cathode layer and the anode layer, and a liquid electrolyte impregnated at least with the separator, characterized in that the liquid electrolyte is the above-explained liquid electrolyte for electrochemical device.

According to the present invention, a lithium secondary battery which can be used at a high voltage can be obtained by using a liquid electrolyte comprising the above-mentioned asymmetric type $BF_3$ complex as a solvent.

Effects of the Present Invention

The present invention attains an effect of providing an asymmetric type $BF_3$ complex which is useful as a solvent for a liquid electrolyte for electrochemical device.

BEST MODE FOR CARRYING OUT THE INVENTION

Figure 1:
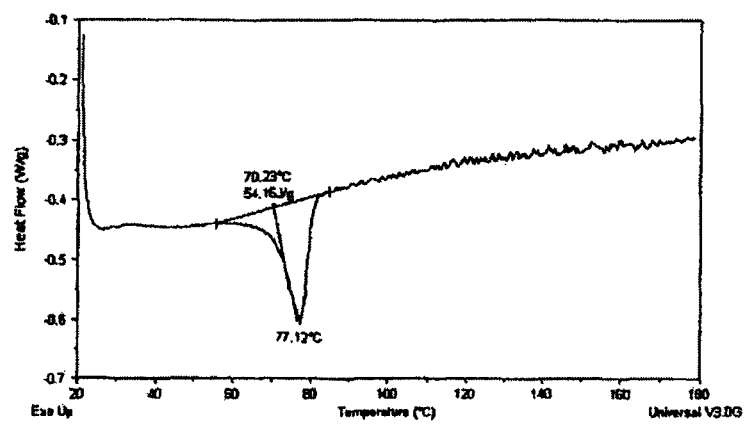
FIG. 1 shows the results of $BF_3$-GBL Complex obtained by using a DSC.

Hereinafter, an asymmetric type $BF_3$ complex, liquid electrolyte for electrochemical device, and a lithium secondary battery of the present invention will be explained.

A. Asymmetric Type $BF_3$ Complex

First, an asymmetric type $BF_3$ complex of the present invention will be explained. The asymmetric type $BF_3$ complex of the present invention is represented by the above-mentioned general formula (1).

In the present invention, an organic molecule (ester) which coordinates to an unoccupied orbital of boron of $BF_3$ has an asymmetric structure to a B—O binding. Thus, a crystal structure is unlikely to be formed, and a complex having a lower melting point and a lower heat of fusion compare to those of similar symmetric type $BF_3$ complex can be obtained. Therefore, the asymmetric type $BF_3$ complex of the present invention is useful, for example, as a solvent for a liquid electrolyte for electrochemical device.

In general, $BF_3$ complexes coordinated with organic molecules at $BF_3$ are solid at room temperature for most cases, and it is necessary to mix the complexes with other organic solvents to use the complexes as solvents for liquid electrolyte for electrochemical devices. At that time, when a melting point is high and a melting energy is strong for a $BF_3$ complex, it is necessary to mix a large amount of organic solvents in order to obtain a liquid mixed solvent at room temperature. Thus, there is a problem of lowering an electrochemical stability, which is a feature of a $BF_3$ complex. In the present invention, an asymmetric type $BF_3$ complex in which symmetric properties of an organic molecule is intentionally broken is used in order to make the formation of a crystal structure difficult. Thereby, it becomes possible to lower a melting point and heat of fusion of the asymmetric type $BF_3$ complex compare to those of similar symmetric type $BF_3$ complex. As a result, an asymmetric type $BF_3$ complex which can be singularly used as a solvent, or an asymmetric type $BF_3$ complex which becomes a liquid by adding a small amount of an organic solvent can be obtained.

That is, the asymmetric type $BF_3$ complex of the present invention is very useful as a solvent for a liquid electrolyte for electrochemical device. Therefore, in the present invention, it is possible to provide a solvent for a liquid electrolyte for electrochemical device represented by the above-mentioned general formula (1).

In the general formula (1), each of $R_1$ and $R_2$ is generally an alkyl group having 1 to 6 carbon atoms. The number of the carbon atoms is preferably within the range of 1 to 3, and more preferably within the range of 1 to 2. Each of $R_1$ and $R_2$ may be an alkyl group not branched or a branched alkyl group, but an alkyl group not branched is preferable. Further, $R_1$ and $R_2$ may be the same of different. In the present invention, $R_1$ and $R_2$ maybe branched or may form a ring. In particular, it is preferable in the present invention that an ester molecule which coordinates to $BF_3$ has a five-membered ring or six-membered ring.

In the present invention, the ester molecule which coordinates to $BF_3$ may be a cyclic ester or a chain ester. As examples of the cyclic ester, gamma-butyrolactone (GBL) and gamma-valerolactone (GVL) can be cited. As examples of the chain ester, ethyl propionate (EP), methyl propionate (MP), ethyl acetate (EA), and methyl acetate (MA) can be cited.

In the present invention, the asymmetric type $BF_3$ complex is a kind of complex selected from the group consisting of the following structural formulae (1a) to (1c). This is because such asymmetric type $BF_3$ complex is particularly useful as a solvent for a liquid electrolyte for electrochemical device. In the present invention, the structural formula (1a) may be referred to "$BF_3$-GBL complex", the structural formula (1b) maybe referred to "$BF_3$-EP complex", and the structural formula (1c) may be referred to "$BF_3$-MP complex".

[Chemical Formula 5]

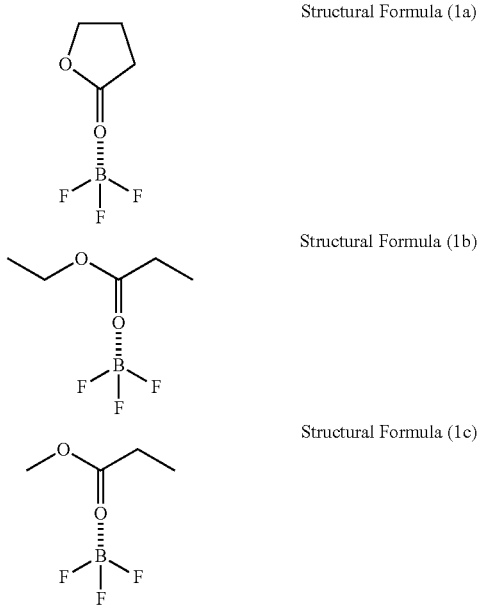

Structural Formula (1a)

Structural Formula (1b)

Structural Formula (1c)

A method of producing an asymmetric type $BF_3$ complex of the present invention is not particularly limited. As an example, a method of aerate a $BF_3$ gas to a raw material ester can be cited. The asymmetric type $BF_3$ complex can be identified, for example, by a carbon-nuclear magnetic resonance method ($^{13}$C-NMR method) and a hydrogen-nuclear magnetic resonance method ($^1$H-NMRmethod).

B. Liquid Electrolyte for Electrochemical Device

Next, a liquid electrolyte for electrochemical device of the present embodiment will be explained. The liquid electrolyte for electrochemical device of the present invention comprises the asymmetric type $BF_3$ complex as a solvent. The liquid electrolyte for electrochemical device can be roughly divided into two embodiments according to the technical structure of the asymmetric type $BF_3$ complex. Hereinafter, the liquid electrolyte for electrochemical device of the present invention will be explained by way of the first and second embodiments.

1. First Embodiment

First, a first embodiment of the liquid electrolyte for electrochemical device of the present invention will be explained. A liquid electrolyte for electrochemical device of the present embodiment comprises the asymmetric type $BF_3$ complex represented by the above-mentioned general formula (1) as a solvent.

According to the present embodiment, a liquid electrolyte for electrochemical device having a wide potential window can be obtained by using the asymmetric type $BF_3$ complex as a solvent. As an acidity of the $BF_3$ part is very strong in the asymmetric type $BF_3$ complex used in the present embodiment, an electron of a coordinating organic molecule (ester) is pulled to the $BF_3$ part. Thus, an oxidation resistance of the organic molecule part in the complex improves and a liquid electrolyte having a wide potential window can be obtained.

Moreover, as explained in the above-mentioned section of "A. Asymmetric Type $BF_3$ Complex", the asymmetric type $BF_3$ complex used in the present embodiment has an asymmetric structure. Thus, it is possible to lower a melting point and heat of fusion of the asymmetric type $BF_3$ complex compare to those of similar symmetric type $BF_3$ complex. Accordingly, for example, even if the asymmetric type $BF_3$ complex is solid at room temperature, the complex can be made to a liquid by adding a small amount of an organic solvent. Therefore, it has an advantage of providing a wide selection in the solvent composition.

The liquid electrolyte for electrochemical device of the present embodiment comprises the above-mentioned asymmetric type $BF_3$ complex represented by the general formula (1) as a solvent. In the present embodiment, the asymmetric type $BF_3$ complex is contained by, generally 10% by weight or more to all of the solvent, preferably 20% by weight or more, and more preferably 50% by weight or more.

Hereinafter, the liquid electrolyte for electrochemical device of the present embodiment will be explained by each technical structure.

(1) Asymmetric Type $BF_3$ Complex

An asymmetric type $BF_3$ complex used in the present embodiment is similar to that explained in the above-mentioned section of "A. Asymmetric Type $BF_3$ Complex".

In particular, in the present embodiment, an ester molecule which coordinates to $BF_3$ of the asymmetric type $BF_3$ complex is preferably a cyclic ester. Specifically, the cyclic ester is preferably GBL or GVL, and more preferably GBL. In other words, in the present embodiment, the asymmetric type $BF_3$ complex is preferably $BF_3$-GBL complex (a complex presented by the above-mentioned structural formula (1a)). Thereby, a liquid electrolyte for electrochemical device significantly excellent in oxidation resistance can be obtained. Specifically, as it will be explained later, an oxidation resistance of the liquid electrolyte for electrochemical device obtained significantly improves when a mixed solvent of DEC and $BF_3$-GBL complex is used compare to a case when a mixed solvent of diethyl carbonate (DEC) and ethylene carbonate (EC) is used.

Further, in the present embodiment, the asymmetric type $BF_3$ complex is preferably a $BF_3$-MP complex (complex represented by the above-mentioned structural formula (1c)). Thereby, a liquid electrolyte for electrochemical device excellent not only in an oxidation resistance but also in reduction-resistance can be obtained. The reason of having excellent reduction-resistance is not necessarily clear, but is thought that the asymmetric type $BF_3$ complex forms a good film by being reducted and decomposed. Substance MP (methyl propionate) becomes a complex by coordinating to $BF_3$ and its oxidation resistance is significantly improved. When the oxidation resistance is improved, the reduction-resistance may sometimes be relatively lowered. However, when a $BF_3$-MP complex is used, a unique effect of improving also the reduction-resistance can be attained.

(2) Solvent for Liquid Electrolyte for Electrochemical Device

In the present embodiment, the asymmetric type $BF_3$ complex represented by the above-mentioned general formula (1) is used as a solvent. For example, when a melting point of the asymmetric type $BF_3$ complex is sufficiently low, solvents used for the liquid electrolyte for electrochemical device may all be asymmetric type $BF_3$ complexes. On the other hand, when a melting point of the asymmetric type $BF_3$ complex is higher than room temperature, solvents other than the asymmetric type $BF_3$ complex is generally used. As the asymmetric type $BF_3$ complex used in the present embodiment has a low heat of fusion, it has an advantage of providing a wide selection in the solvent composition. The preferable solvent composition is the same as those explained above.

As examples of solvents other than the asymmetric type $BF_3$ complex, carbonates such as ethylene carbonate (EC), propylene carbonate (PC), dimethyl carbonate (DMC), diethyl carbonate (DEC), and ethylmethyl carbonate (EMC); ethers such as dimethyl ether, diethyl ether, tetrahydrofuran (THF), and methyltetrahydrofuran; nitriles such as methoxypropionitrile and acetonitrile; esters such as methyl acetate; amines such as triethylamine; alcohols such as methanol; and ketones such as acetone, can be cited. Among them, carbonates are preferable. Further, an organic molecule which coordinates to $BF_3$ of the asymmetric type $BF_3$ complex can be used as solvents other than the asymmetric type $BF_3$ complex.

(3) Electrolyte of Liquid Electrolyte for Electrochemical Device

An electrolyte used in the present embodiment is not particularly limited as long as it is dissolved in a solvent which contains the asymmetric type $BF_3$ complex. The type of the electrolyte varies depending on the use of the liquid electrolyte. As examples, Li salts, Na salts, and quaternary ammonia salts can be cited, and Li salts are preferable among them. This is because they can be used in lithium secondary batteries.

As the Li salts, a general Li salts may be used and not particularly limited. For example, $LiN(SO_2CF_3)_2$ (in some cases also referred to LiTFSI), $LiN(SO_2C_2F_5)_2$ (in some cases also referred to LiBETI), $LiClO_4$, $LiBF_4$, and $LiPF_6$ can be cited. Among them, $LiN(SO_2CF_3)_2$ and $LiN(SO_2C_2F_5)_2$ are preferable. This is because the lithium imide salts such as LiTFSI and LiBETI have high decomposition temperature and can restrain the generation of hydrogen fluoride (HF).

A density of the electrolyte of the liquid electrolyte for electrochemical device is not particularly limited, and it is the same as the density of a general electrolyte. Although it is not particularly limited, it is normally about 1 mol/L.

(4) Others

As examples of an application of the liquid electrolyte for electrochemical device of the present embodiment, a secondary battery, capacitor, or sensor can be cited. Among them, a secondary battery and capacitor are preferable, and a secondary battery is particularly preferable. Further, even among the secondary batteries, it is preferable to use the liquid electrolyte for electrochemical device of the present embodiment as a lithium secondary battery.

2. Second Embodiment

Next, a second embodiment of a liquid electrolyte for electrochemical device of the present invention will be explained. The liquid electrolyte for electrochemical device of the present embodiment comprises an asymmetric type $BF_3$ complex represented by the below-mentioned general formula (2) as a solvent:

[Chemical Formula 6]

General Formula (2)

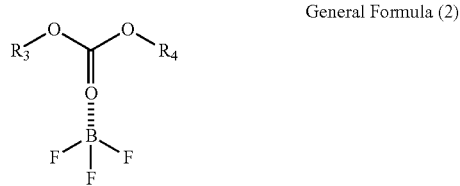

(in the general formula (2), each of $R_3$ and $R_4$ is an alkyl group having 1 to 5 carbon atoms and is a different alkyl group).

According to the present embodiment, a liquid electrolyte for electrochemical device having a wide potential window can be obtained by using the asymmetric type $BF_3$ complex as a solvent. As an acidity of the $BF_3$ part is very strong in the asymmetric type $BF_3$ complex used in the present embodiment, an electron of a coordinating organic molecule (carbonate) is pulled to the $BF_3$ part. Thus, an oxidation resistance of the organic molecule part in the complex improves and a liquid electrolyte having a wide potential window can be obtained.

Moreover, as explained in the above-mentioned section of "A. Asymmetric Type $BF_3$ Complex", the asymmetric type $BF_3$ complex used in the present embodiment also has an asymmetric structure. Thus, it is possible to lower a melting point and heat of fusion of the asymmetric type $BF_3$ complex compare to those of similar symmetric type $BF_3$ complex. Accordingly, for example, even if the asymmetric type $BF_3$ complex is solid at room temperature, the complex can be made to liquid by adding a small amount of an organic solvent. Therefore, it has an advantage of providing a wide selection in the solvent composition.

The liquid electrolyte for electrochemical device of the present embodiment comprises the above-mentioned asymmetric type $BF_3$ complex represented by the general formula (2) as a solvent. In the present embodiment, the asymmetric type $BF_3$ complex is contained by, generally 10% by weight or more to all of the solvent, preferably 20% by weight or more, and more preferably 50% by weight or more.

Hereinafter, the liquid electrolyte for electrochemical device of the present embodiment will be explained by each technical structure.

(1) Asymmetric Type $BF_3$ Complex

First, an asymmetric type $BF_3$ complex used in the present embodiment will be explained. The asymmetric type $BF_3$ complex used in the present embodiment is represented by the above-mentioned general formula (2). As the asymmetric type $BF_3$ complex used in the present embodiment has an asymmetric structure, it is very useful as a solvent for a liquid electrolyte for electrochemical device similarly to the case of the above-explained first embodiment. Therefore, it is possible in the present embodiment to provide the solvent for a liquid electrolyte for electrochemical device represented by the above-mentioned general formula (2).

In the general formula (2), each of $R_3$ and $R_4$ is generally an alkyl group having 1 to 5 carbon atoms. The number of the carbon atoms is preferably within the range of 1 to 3, and more preferably within the range of 1 to 2. Each of $R_3$ and $R_4$ may be an alkyl group not branched or a branched alkyl group, but an alkyl group not branched is preferable. Further, $R_3$ and $R_4$ are different alkyl group. This is because, if they are the same alkyl group, the asymmetric type $BF_3$ complex cannot have an asymmetric structure.

In particular, in the present embodiment, the asymmetric type $BF_3$ complex is preferably a complex represented by the below-mentioned structural formula (2a). This is because such asymmetric type $BF_3$ complex is useful as a solvent for a liquid electrolyte for electrochemical device. In the present embodiment, the structural formula (2a) may sometimes be referred as "$BF_3$-EMC complex".

[Chemical Formula 7]

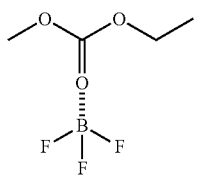

Structural Formula (2a)

A method of producing an asymmetric type $BF_3$ complex of the present embodiment is not particularly limited. As an example, a method of aerate a $BF_3$ gas to a raw material carbonate can be cited. The asymmetric type $BF_3$ complex can be identified, for example, by a carbon-nuclear magnetic resonance method ($^{13}$C-NMR method) and a hydrogen-nuclear magnetic resonance method ($^1$H-NMR method).

(2) Solvent for Liquid Electrolyte for Electrochemical Device

In the present embodiment, an asymmetric type $BF_3$ complex represented by the above-mentioned general formula (2) is used as a solvent. For example, when a melting point of the asymmetric type $BF_3$ complex is sufficiently low, solvents used for the liquid electrolyte for electrochemical device may all be asymmetric type $BF_3$ complexes. On the other hand, when a melting point of the asymmetric type $BF_3$ complex is higher than room temperature, solvents other than the asymmetric type $BF_3$ complex is generally used. As the asymmetric type $BF_3$ complex used in the present embodiment has a low heat of fusion, it has an advantage of providing a wide selection in the solvent composition. The preferable solvent composition is the same those as explained above.

As solvents other than the asymmetric type $BF_3$ complex is the same to those explained in the above-mentioned section of "1. First Embodiment", explanation here is omitted. Further, the electrolyte, the application of the liquid electrolyte for electrochemical device, and other factors of the present embodiment are the same to those explained in the above-mentioned section of "1. First Embodiment", explanation here is omitted.

C. Lithium Secondary Battery

Next, a lithium secondary battery of the present invention will be explained. The lithium secondary battery of the present invention comprises: a cathode layer containing a cathode active material, an anode layer containing an anode active material, a separator provided between the cathode layer and the anode layer, and a liquid electrolyte impregnated at least with the separator, characterized in that the liquid electrolyte is the liquid electrolyte for electrochemical device explained above.

According to the present invention, a lithium secondary battery which can be used at a high voltage can be obtained by using a liquid electrolyte comprising the above-mentioned asymmetric type $BF_3$ complex as a solvent.

The lithium secondary battery of the present invention comprises at least a cathode layer, an anode layer, a separator, and a liquid electrolyte. As the liquid electrolyte is the same to that explained in the above-mentioned section of "B. Liquid Electrolyte for Electrochemical Device", explanation here is omitted.

The cathode layer used in the present invention contains at least a cathode active material. As examples of the cathode active material, $LiCoO_2$, $LiMn_2O_4$, $LiNiO_2$, $LiNi_{0.8}Co_{0.2}O_2$, $LiNi_{1/3}Mn_{1/3}Co_{1/3}O_2$, $LiNi_{0.5}Mn_{0.5}O_2$, $LiNi_{0.5}Mn_{1.5}O_4$, $LiCoPO_4$, $LiMnPO_4$, $LiFePO_4$ can be cited. Among them, $LiCoO_2$ is preferable. Further, the cathode active material generally contains a conductive material and a binder. As examples of the conductive material, carbon black and acetylene black can be cited. As examples of the binder, fluorine-based resins such as polyvinylidene fluoride (PVDF), polytetrafluoroethylene (PTFE), and ethylenetetrafluoroethylene (ETFE) can be cited. Further, the lithium secondary battery of the present invention generally comprises a cathode active material which corrects current of a cathode layer. As examples of a material for the cathode current collector, aluminum, stainless, nickel, iron, and titanium can be cited.

The anode layer used in the present invention contains at least an anode active material. As examples of the anode active material, metal lithium, a lithium alloy, metal oxide, metal sulfide, metal nitride, and carbon material such as graphite can be cited. Among them, graphite is preferable. The anode layer may contain a conductive material and a binder as needed. As for the conductive material and the binder, the same materials as the cathode layer can be used. Further, the lithium secondary battery of the present invention normally comprises an anode current collector which corrects currents of the anode layer.

As examples of a material for the anode current collector, copper, stainless, and nickel can be cited. As for the separator used in the present invention, the same materials as the separator substrates used in general lithium secondary batteries can be used, and thus, not particularly limited. For example, resins such as polyethylene (PE), polypropylene (PP), polyester, cellulose, and polyamide can be cited. Among them, polyethylene and polypropylene are preferable. Further, a shape of a battery case used in the present invention is not particularly limited as long as it can store the above-mentioned cathode layer, anode layer, and a separator. As specific example, a cylindrical type, a square type, a coin type, and a laminate type can be cited.

The present invention is not restricted to the foregoing embodiments. The embodiments are provided only for the purpose of illustration, and all that has a substantially same configuration with a technical idea described in the scope of claims of the invention and exerts a similar advantage is contained in a technical range of the invention.

EXAMPLES

The present invention will be further specifically explained by way of examples.

Example 1-1

Prepared as a raw material ester was gamma-butyrolactone (GBL) and it was aerated with a $BF_3$ gas in 0° C. nitrogen atmosphere for 20 minutes or longer. A white liquid was obtained consequently. The obtained liquid was filtered and a solid was removed, and thereby, a white $BF_3$-GBL complex was obtained.

Next, a melting point and a heat of fusion of the obtained $BF_3$-GBL complex were measured. Measurement was conducted by sealing the $BF_3$-GBL complex in a SUS closed container, using a differential scanning calorimeter (DSC), and setting the temperature rising conditions to 2° C./minute and the upper limit of the temperature to 180° C. As a result, as shown in FIG. 1, a melting point of the $BF_3$-GBL complex was 70.23° C., and a heat of fusion thereof was 54.16 J/g.

Example 1-2

A $BF_3$-EP complex was obtained in the same manner as in Example 1-1 except that ethyl propionate (EP) was used as a raw material ester.

Figure 2:
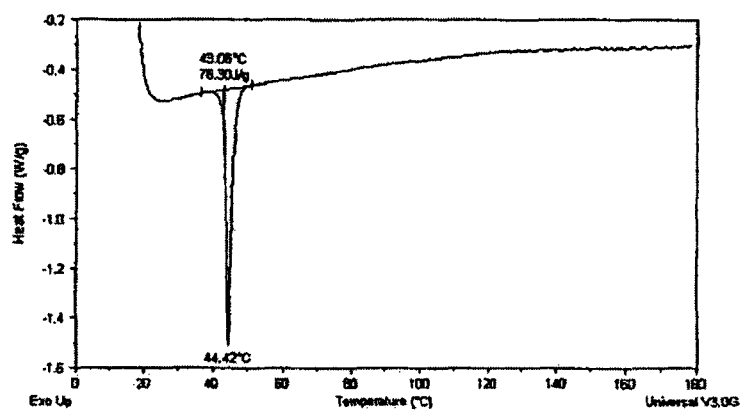
FIG. 2 shows the results of $BF_3$-EP Complex obtained by using a DSC.

Next, a melting point and a heat of fusion of the obtained $BF_3$-EP complex were measured in the same manner as in Example 1-1. As shown in FIG. 2, a melting point of the $BF_3$-EP complex was 43.06° C., and a heat of fusion thereof was 76.30 J/g.

Example 1-3

A $BF_3$-MP complex was synthesized in the same manner as in Example 1-1 except that methyl propionate (MP) was used as a raw material ester. In the present example, the obtained liquid was filtered while it was cooled down after aerated with a $BF_3$ gas, and a solid was removed. The obtained $BF_3$-MP complex was liquid at room temperature.

Example 1-4

A $BF_3$-EMC complex was obtained in the same manner as in Example 1-1 except that ethyl methyl carbonate (EMC) was used as a raw material carbonate instead of raw material ester.

Figure 3:
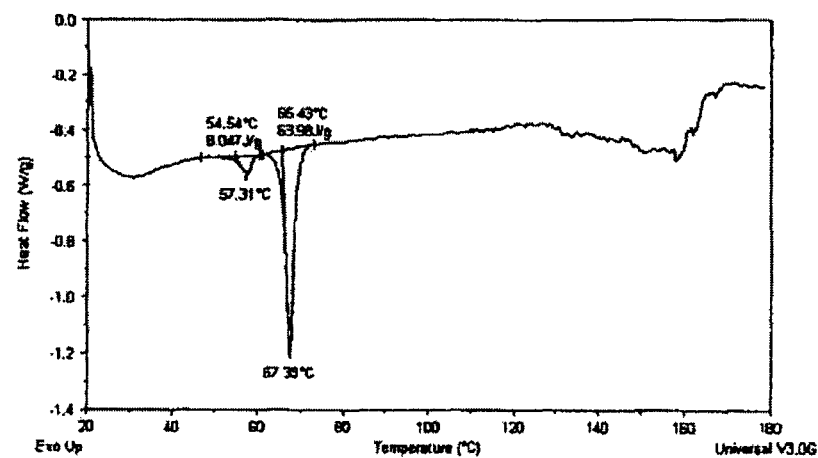
FIG. 3 shows the results of $BF_3$-EMC Complex obtained by using a DSC.

Next, a melting point and a heat of fusion of the obtained $BF_3$-EMC complex were measured in the same manner as in Example 1-1. As shown in FIG. 3, a melting point of the $BF_3$-EMC complex was 65.43° C., and a heat of fusion thereof was 63.98 J/g.

Comparative Example 1-1

A $BF_3$-DMC complex was obtained in the same manner as in Example 1-1 except that diethyl carbonate (DMC) was used as a symmetric type organic molecule.

Next, a melting point and a heat of fusion of the obtained $BF_3$-DMC complex were measured in the same manner as in Example 1-1. A melting point of the $BF_3$-DMC complex was 110.79° C., and a heat of fusion thereof was 125.5 J/g.

Comparative Example 1-2

A $BF_3$-DEC complex was obtained in the same manner as in Example 1-1 except that diethyl carbonate (DMC) was used as a symmetric type organic molecule.

Next, a melting point and a heat of fusion of the obtained $BF_3$-DEC complex were measured in the same manner as in Example 1-1. A melting point of the $BF_3$-DEC complex was 58.45° C., and a heat of fusion thereof was 156.4 J/g.

The above-mentioned results are shown in below Table 1.

TABLE 1

| | Complex | Melting Point (° C.) | Heat of Fusion (J/g) |
|---|---|---|---|
| Example 1-1 | $BF_3$-GBL | 70.23 | 54.16 |
| Example 1-2 | $BF_3$-EP | 43.06 | 76.30 |
| Example 1-3 | $BF_3$-MP | Room Temperature or Lower | — |
| Example 1-4 | $BF_3$-EMC | 65.43 | 63.98 |
| Comparative Example 1-1 | $BF_3$-DMC | 110.79 | 125.5 |
| Comparative Example 1-2 | $BF_3$-DEC | 58.45 | 156.4 |

As apparent from Table 1, all complexes obtained in examples showed low melting points and heat of fusion. In contrast, the symmetric type organic molecule of Comparative Example 1-1 showed high value in both of melting point and heat of fusion. Further, the symmetric type organic molecule of Comparative Example 1-2 showed low melting point, but also showed high heat of fusion, so that it was necessary to add a large amount of other organic solvent to obtain a liquid electrolyte in a liquid state at room temperature.

Example 2-1

A $BF_3$-GBL complex obtained in Example 1-1 and diethyl carbonate (DEC) was mixed so as the mol ratio thereof becomes 1:1, and a homogenous mixed solvent was obtained. Subsequently, $LiPF_6$ was dissolved by 1M to the obtained mixed solvent and a liquid electrolyte for electrochemical device was obtained.

Comparative Example 2-1

A liquid electrolyte for electrochemical device was obtained in the same manner as in Example 2-1 except that ethylene carbonate (EC) was used instead of a $BF_3$-GBL complex.

[Evaluation]

The oxidation potential of the respective liquid electrolyte for electrochemical device obtained in Example 2-1 and Comparative Example 2-1 were measured. Measurement was conducted by using a three electrode cell provided with glassy carbon for a working electrode, lithium metals for a counter electrode and a reference electrode, and under a linear sweep voltammetric technique. At the time of measuring, potential of the working electrode was swept from the immersed potential to the high potential side. The sweep speed was 5 m $Vsec^{-1}$.

Figure 4:
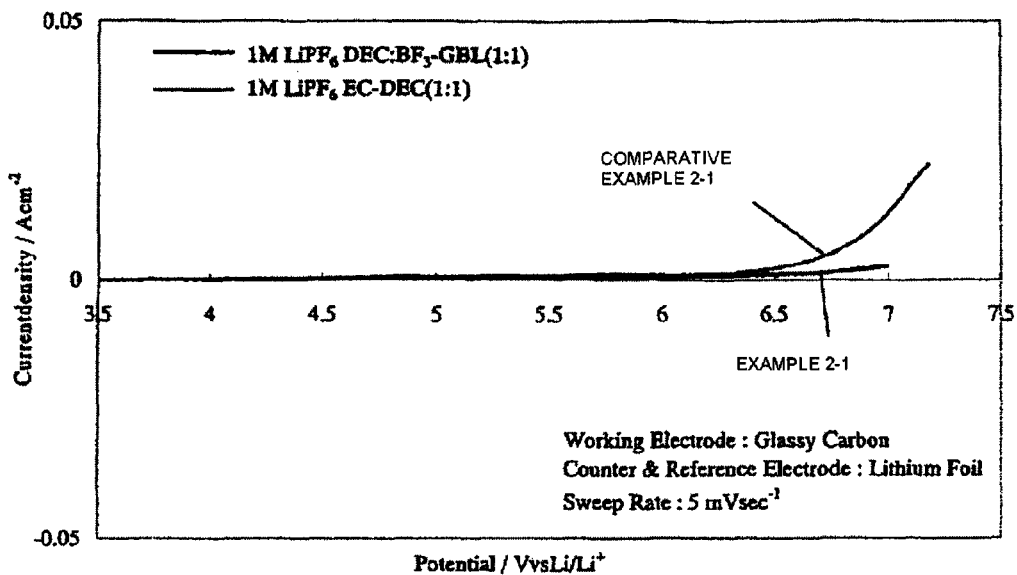
FIG. 4 shows LSV curves of the liquid electrolytes for electrochemical device obtained in Example 2-1 and Comparative Example 2-1.

The results (LSV curves) are shown in FIG. 4. As shown in FIG. 4, with the liquid electrolyte for electrochemical device of Comparative Example 2-1, elevation in current value were confirmed from the potential of about 6.5 VvsLi/Li$^+$. When glassy carbon is used for a working electrode, no particularly active RedOx series is present in electrodes and a solution. Thus, the current confirmed here is thought to be caused by oxidative decomposition of the liquid electrolyte itself. In contrast, with the liquid electrolyte for electrochemical device of Comparative Example 2-1, no substantial current was flowing even at potentials higher than 6.5 VvsLi/Li$^+$. Thus, the liquid electrolyte for electrochemical device of the present invention was found excellent in oxidation resistance.

Example 2-2

A BF$_3$-MP complex obtained in Example 1-3 and diethyl carbonate (DEC) was mixed so as the mol ratio thereof becomes 1:1, and a homogenous mixed solvent was obtained. Subsequently, LiPF$_6$ was dissolved by 1M to the obtained mixed solvent and a liquid electrolyte for electrochemical device was obtained.

Comparative Example 2-2

A liquid electrolyte for electrochemical device was obtained in the same manner as Example 2-2 except that ethylene carbonate (EC) was used instead of a BF$_3$-MP complex.

[Evaluation]

The reduction potential of the respective liquid electrolyte for electrochemical device obtained in Example 2-2 and Comparative Example 2-2 were measured. Measurement was conducted by using a three electrode cell provided with glassy carbon for a working electrode, lithium metals for a counter electrode and a reference electrode, and under a linear sweep voltammetric technique. At the time of measuring, potential of the working electrode was swept from the immersed potential to the low potential side. The sweep speed was 5 mVsec$^{-1}$.

Figure 5:
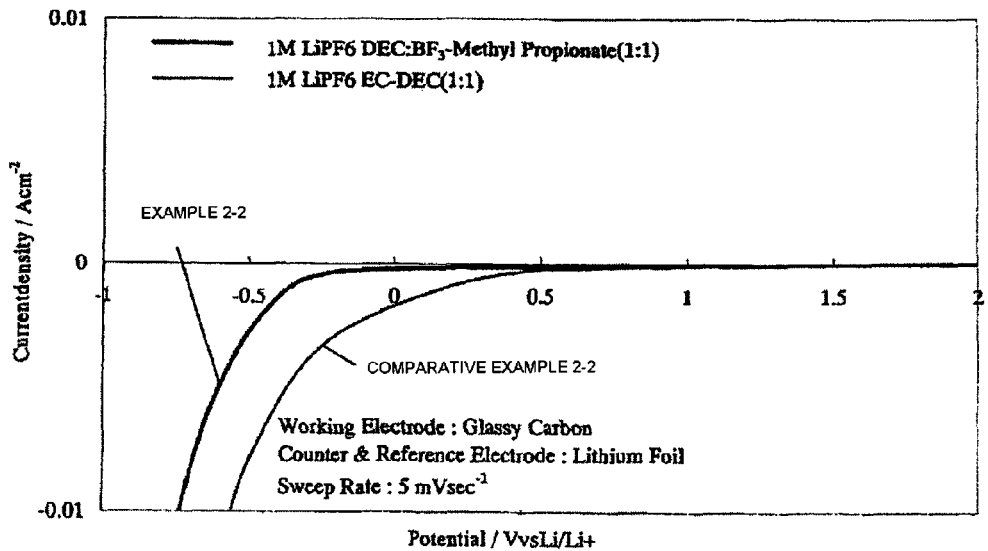
FIG. 5 shows LSV curves of the liquid electrolytes for electrochemical device obtained in Example 2-2 and Comparative Example 2-2

The results (LSV curves) are shown in FIG. 5. As shown in FIG. 5, with the liquid electrolyte for electrochemical device of Comparative Example 2-2, reduction current were confirmed from the potential of about 0.5 VvsLi/Li$^+$. This is thought to be caused by reductive degradation of the liquid electrolyte itself. In contrast, with the liquid electrolyte for electrochemical device of Comparative Example 2-2, no substantial current was flowing until 0.2 VvsLi/Li$^+$. Thus, it was confirmed that the reduction-resistance of the liquid electrolyte was improved.

Example 2-3

A BF$_3$-EMC complex obtained in Example 1-4 and EMC was mixed so as the mol ratio thereof becomes 1:1, and a homogenous mixed solvent was obtained. Subsequently, LiTFSI was dissolved by 1M to the obtained mixed solvent and a liquid electrolyte for electrochemical device was obtained.

Comparative Example 2-3

A liquid electrolyte for electrochemical device was obtained in the same manner as Example 2-3 except that only EMC was used as a solvent.

[Evaluation]

The oxidation potential of the respective liquid electrolyte for electrochemical device obtained in Example 2-3 and Comparative Example 2-3 were measured. Measurement was conducted by using a three electrode cell provided with glassy carbon for a working electrode, lithium metals for a counter electrode and a reference electrode, and under a linear sweep voltammetric technique. At the time of measuring, potential of the working electrode was swept from the immersed potential to the high potential side. The sweep speed was 5 mVsec$^{-1}$.

Figure 6:
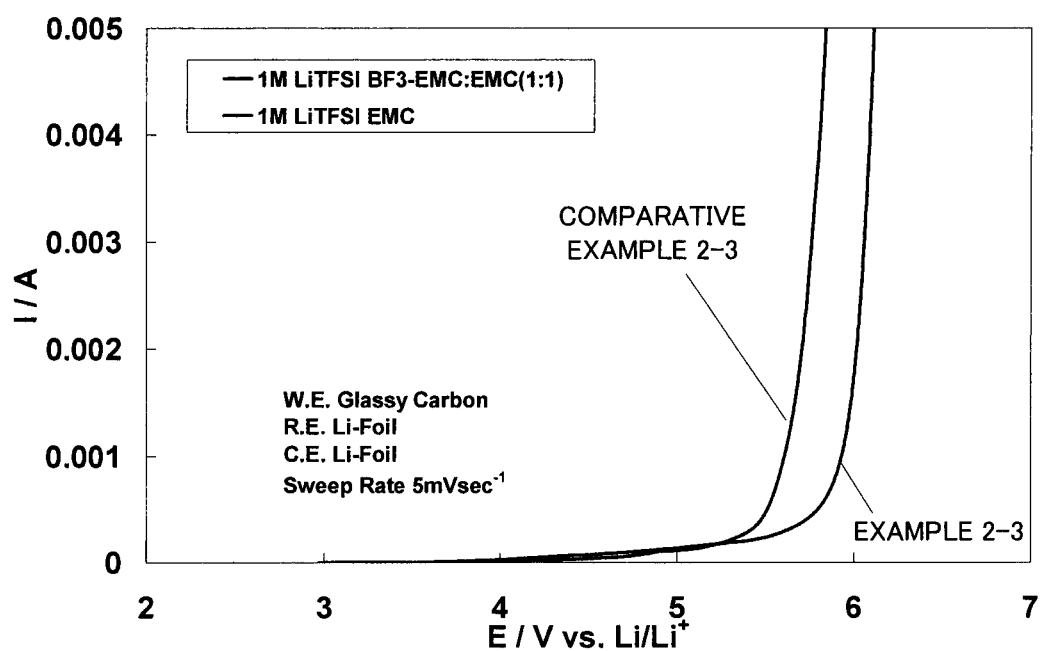
FIG. 6 shows LSV curves of the liquid electrolytes for electrochemical device obtained in Example 2-3 and Comparative Example 2-3.

The results (LSV curves) are shown in FIG. 6. As shown in FIG. 6, with the liquid electrolyte for electrochemical device of Comparative Example 2-3, elevation in current value were confirmed from the potential of about 5.2 VvsLi/Li$^+$. In contrast, with the liquid electrolyte for electrochemical device of Example 2-3, no substantial current was flowing until about 5.6 VvsLi/Li$^+$. Thus, the liquid electrolyte for electrochemical device of the present invention was found excellent in oxidation resistance.

The invention claimed is:

1. A liquid electrolyte for electrochemical device comprising an asymmetric type BF$_3$ complex represented by the following general formula (1), as a solvent, with 50% by weight or more with respect to all solvent:

[Chemical Formula 1]

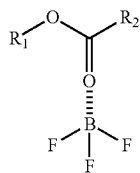

General Formula (1)

(in the general formula (1), each of R$_1$ and R$_2$ is an alkyl group having 1 to 6 carbon atoms and may be the same or different, and R$_1$ and R$_2$ may be branched or may form a ring).

2. The liquid electrolyte for electrochemical device according to claim 1, wherein the asymmetric type BF$_3$ complex is a kind of complex selected from the group consisting of the following structural formulae (1a) to (1c):

[Chemical Formula 2]

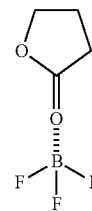

Structural Formula (1a)

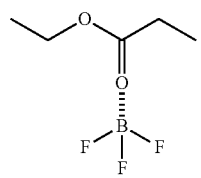

Structural Formula (1b)

-continued

Structural Formula (1c)

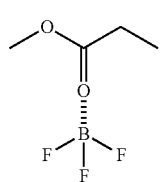

3. A lithium secondary battery comprising:
a cathode layer containing a cathode active material,
an anode layer containing an anode active material,
a separator provided between the cathode layer and the anode layer, and
a liquid electrolyte impregnated at least with the separator,
wherein the liquid electrolyte is the liquid electrolyte for electrochemical device according to claim 1.

4. The lithium secondary battery according to claim 3, wherein the cathode active material is a kind of active material selected from the group consisting of $LiCoO_2$, $LiMn_2O_4$, $LiNiO_2$, $LiNi_{0.8}Co_{0.2}O_2$, $LiNi_{1/3}Mn_{1/3}Co_{1/3}O_2$, $LiNi_{0.5}Mn_{0.5}O_2$, $LiNi_{0.5}Mn_{1.5}O_4$, $LiCoPO_4$, $LiMnPO_4$, $LiFePO_4$.

* * * * *